(12) United States Patent
Davies et al.

(10) Patent No.: US 11,235,106 B2
(45) Date of Patent: Feb. 1, 2022

(54) INJECTION DEVICE WITH DOSE INDICATOR MECHANISM

(71) Applicant: NORTON HEALTHCARE LIMITED, West Yorkshire (GB)

(72) Inventors: James Alexander Davies, Cambridgeshire (GB); Oliver Hart, Cambridgeshire (GB); Karl James Hewson, Cambridgeshire (GB); Joshua Arieh Shenker, Cambridgeshire (GB)

(73) Assignee: Norton Healthcare Limited, Castleford (GB)

( * ) Notice: Subject to any disclaimer, the term of this patent is extended or adjusted under 35 U.S.C. 154(b) by 227 days.

(21) Appl. No.: 16/332,182

(22) PCT Filed: Sep. 11, 2017

(86) PCT No.: PCT/EP2017/072717
§ 371 (c)(1),
(2) Date: Mar. 11, 2019

(87) PCT Pub. No.: WO2018/046718
PCT Pub. Date: Mar. 15, 2018

(65) Prior Publication Data
US 2019/0217014 A1 Jul. 18, 2019

(30) Foreign Application Priority Data

Sep. 12, 2016 (GB) ..................... 1615453

(51) Int. Cl.
*A61M 5/315* (2006.01)
*A61M 5/20* (2006.01)
(Continued)

(52) U.S. Cl.
CPC .......... *A61M 5/31541* (2013.01); *A61M 5/20* (2013.01); *A61M 5/31535* (2013.01);
(Continued)

(58) Field of Classification Search
CPC .......... A61M 5/31541; A61M 5/31535; A61M 5/20; A61M 5/31553; A61M 5/31583;
(Continued)

(56) References Cited

U.S. PATENT DOCUMENTS 5,279,585 A * 1/1994 Balkwill ............. A61M 5/3158
222/309
8,672,898 B2 3/2014 Enggaard
2006/0153693 A1 7/2006 Fiechter et al.

FOREIGN PATENT DOCUMENTS

EP 0554995 A1 8/1993
WO 2006/045528 A1 5/2006
(Continued)

OTHER PUBLICATIONS

International Search Report and Written Opinion; PCT/EP2017/072717 dated Jan. 2, 2018, 18 pages.

*Primary Examiner* — Deanna K Hall
(74) *Attorney, Agent, or Firm* — BakerHostetler

(57) ABSTRACT

An injection device comprises a housing, a dose indicator positioned within the housing and a dose selector operatively connectable to the dose indicator. The dose selector and the dose indicator are capable of cooperating with one another to set a dose to be ejected from the injection device. The dose indicator comprises an odometer including: i. a units (218) wheel operatively connected to the dose selector so that rotation of the dose selector also rotates the units wheel, and ii. a tens wheel (219) selectively engageable with the units wheel so that rotation of the units wheel also rotates the tens wheel. The dose indicator further comprises an axially-moveable shuttle lock (222) rotationally locked to the tens wheel and selectively engageable with the units wheel and the housing. The tens wheel is selectively engageable with the units wheel via said shuttle lock and, when the
(Continued)

tens wheel is not engaged with the units wheel, the shuttle lock is rotationally locked to the housing.

20 Claims, 20 Drawing Sheets

(51) Int. Cl.
*G06M 1/04* (2006.01)
*A61M 5/24* (2006.01)
*A61M 5/31* (2006.01)

(52) U.S. Cl.
CPC .... *A61M 5/31553* (2013.01); *A61M 5/31583* (2013.01); *A61M 5/31593* (2013.01); *G06M 1/042* (2013.01); *A61M 5/24* (2013.01); *A61M 5/3157* (2013.01); *A61M 2005/3126* (2013.01)

(58) Field of Classification Search
CPC .. A61M 5/31593; A61M 5/24; A61M 5/3157; A61M 2005/3126; G06M 1/042
See application file for complete search history.

(56) References Cited

FOREIGN PATENT DOCUMENTS

| | | |
|---|---|---|
| WO | 2013/087574 A1 | 6/2013 |
| WO | 2013/178372 A1 | 12/2013 |
| WO | 2014/166908 A1 | 10/2014 |
| WO | 2015/007820 A1 | 1/2015 |
| WO | 2015/181141 A1 | 12/2015 |
| WO | 2016/001299 A1 | 1/2016 |
| WO | 2016/055438 A1 | 4/2016 |

\* cited by examiner

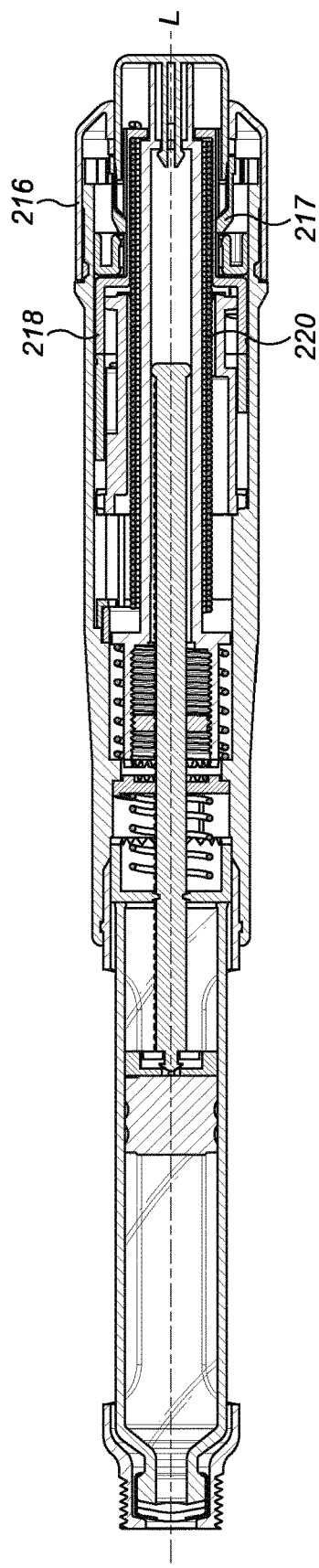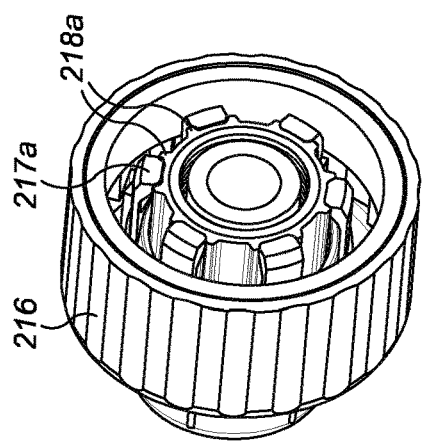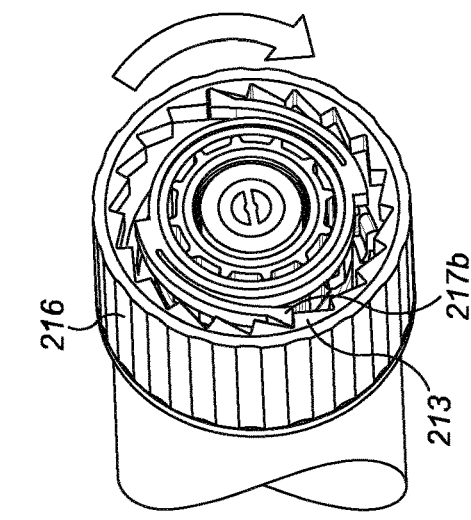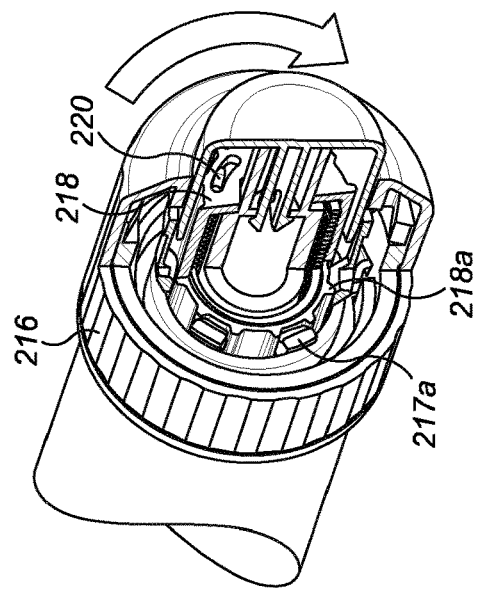

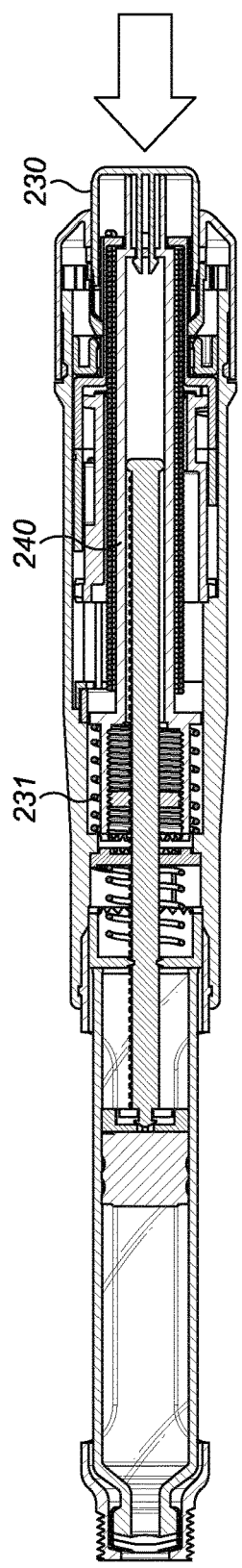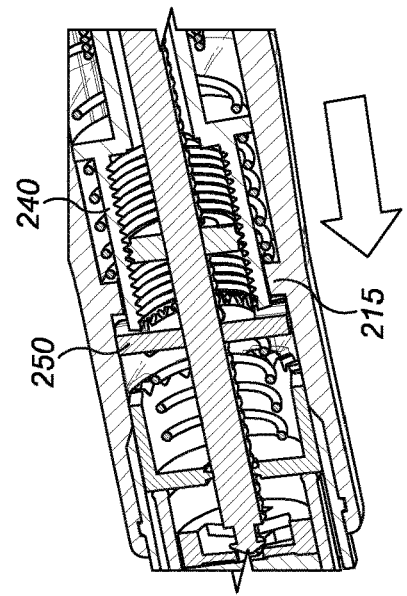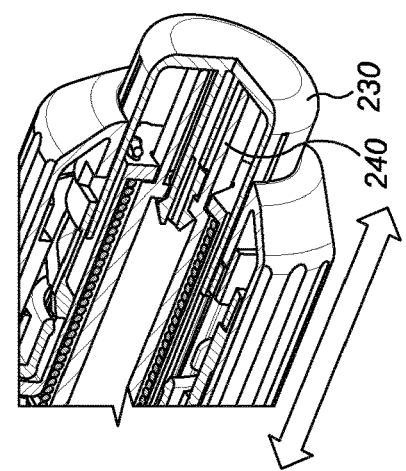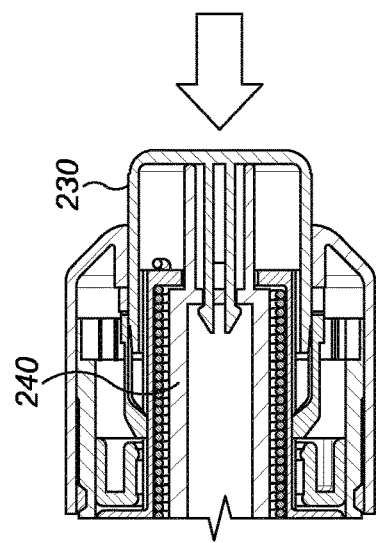

INJECTION DEVICE WITH DOSE INDICATOR MECHANISM

CROSS-REFERENCE TO RELATED APPLICATIONS

This application is the National Stage of International Patent Application No. PCT/EP2017/072717, filed Sep. 11, 2017, which claims priority from Great Britain Patent Application No. 1615453.6, filed Sep. 12, 2016, the entire contents of both of which applications are incorporated herein by reference.

This disclosure relates to the field of dose indicator mechanisms for injection devices, preferably to dose indicator mechanisms having a torsion spring for assisting injection of a dose of medicament from an injection device.

BACKGROUND

Certain injection devices are required to have a visual indicator for the user so that the correct dose of medicament can be set and observed. This dose indicator commonly takes the form of a number sleeve, an example of which is described in U.S. Pat. No. 8,672,898. A rotatable sleeve with numbers printed along a helical line can be inspected through a window in the housing of the device, the window showing only one of the numbers at a time which corresponds to the dose set. However, U.S. Pat. No. 8,672,898 uses a linear compression spring. An example of a number sleeve in an injection device using a torsion spring is described in WO2014/166908.

A disadvantage of using a number sleeve to indicate the dose is that the indicator area takes up a relatively large portion of the device and is generally centrally located, as illustrated in FIG. 2 of WO2014/166908. Desirably, the dose indicator needs to avoid areas of the device where the user will grip the device, so that the user's fingers do not obscure the dose indication.

An alternative type of dose indication is provided by an odometer or "units and tens" wheels or ciphers arrangement in place of a number sleeve. An example is given in WO2006/045528. Two wheels, each carrying the ten ciphers from "0" to "9" are used wherein the "tens" wheel is rotated one increment every time the "units" wheel is rotated one full revolution so that the two wheels between them can form all of the numbers from "00" to "99" in a display window. An odometer has an advantage over a number sleeve as a dose indicator in that it can be located further rearwardly towards the proximal end of the device where it is less likely to interfere with the user's finger position.

U.S. Pat. No. 5,279,585 describes a medication delivery pen having a units counter ring and a tens counter ring. The units counter ring is splined to an axially-moveable plunger and is also secured to a dose adjusting knob such that rotation of the dose adjusting knob causes a corresponding rotation of the units counter ring. Grooves on the tens counter ring are engageable with a zero detection clip. A transmission key is provided on the units counter ring for engaging and disengaging the units and tens counter rings together.

WO2013/087574 describes another example of an injector pen having an odometer, in the form of two different scale drums rotatably mounted with respect to the housing of the injection device and moveable axially with respect to the housing when rotated.

BRIEF SUMMARY OF THE DISCLOSURE

In accordance with an aspect of the present invention there is provided an injection device comprising:

a. a housing;
b. a dose indicator positioned within the housing; and
c. a dose selector operatively connectable to the dose indicator, the dose selector and the dose indicator being capable of cooperating with one another to set a dose to be ejected from the injection device, wherein the dose indicator comprises an odometer including:
    a units wheel operatively connected to the dose selector so that rotation of the dose selector also rotates the units wheel, and
    a tens wheel selectively engageable with the units wheel so that rotation of the units wheel also rotates the tens wheel, wherein the dose indicator further comprises an axially-moveable shuttle lock rotationally locked to the tens wheel and selectively engageable with the units wheel and the housing;

wherein the tens wheel is selectively engageable with the units wheel via said shuttle lock; and wherein, when the tens wheel is not engaged with the units wheel, the shuttle lock is rotationally locked to the housing.

The tens wheel is engaged with the units wheel when it is desired to increment the tens display, usually once every ten increments of the units wheel. The shuttle lock is always rotationally locked to the tens wheel. Therefore, by rotationally locking the shuttle lock to the housing when the tens wheel is not engaged with the units wheel (i.e. between increments of the tens wheel), the risk of the tens wheel moving unintentionally and undesirably is reduced. This facilitates a more accurate display of the dose.

In an embodiment, the shuttle lock is generally cylindrical, having a forward section and a rear section, the forward section having a greater diameter than a diameter of the rear section.

In an embodiment, one of the shuttle lock and tens wheel includes an axially-extending keyway and the other of the shuttle lock and tens wheel includes a radially projecting key for engaging in said keyway in order to rotationally lock the shuttle lock to the tens wheel. Preferably, the shuttle lock and tens wheel are axially moveable with respect to one another when said key is engaged in said keyway.

In an embodiment, the shuttle lock includes a set of peripheral teeth arranged in one axial location on an outer surface thereof, the peripheral teeth being capable of selectively engaging one or more formations on an internal surface of the housing. Preferably, the peripheral teeth are substantially equally spaced around a circumference of the shuttle lock at said axial location.

In an embodiment, the peripheral teeth each have a forward surface and a rear surface, the forward and rear surfaces being capable of engaging first and second formations respectively on the internal surface of the housing. Preferably, said first formations comprise ribs for engaging the forward surface of said peripheral teeth and said second formations comprise dogs for engaging the rear surface of said peripheral teeth.

When the tens wheel is not engaged with the units wheel, the shuttle lock may be rotationally locked to the housing by said dogs engaging the forward surface of said peripheral teeth.

In an embodiment, said units wheel includes a drive dog having a cam surface capable of selectively engaging a dog on said shuttle lock to effect axial movement of said shuttle lock.

The units wheel may include an axially-extending spline capable of engaging teeth on an end surface of said shuttle lock so as to selectively rotationally lock the units wheel and shuttle lock together.

In an embodiment, the internal surface of the housing further comprises an axially-extending rib for limiting rotation of the tens wheel. Preferably, said tens wheel includes a rotary endstop feature for engaging said axially-extending rib. The tens wheel may include two of said rotary endstop features, for maximum and minimum dose limiting respectively. Preferably, each of said rotary endstop features are capable of engaging said axially-extending rib.

In an embodiment, the units wheel and tens wheel are each marked with a sequence of numbers or symbols, at least one of the numbers or symbols being visible through an aperture or window in the housing.

The injection device may further comprise a medicament container, where the medicament container may comprise a pre-filled syringe or cartridge. The injection device may further comprise a medicament contained in the medicament container. In certain embodiments, the medicament may be selected from the group comprising: antipsychotic substances including risperidone, hormones, antitoxins, substances for the control of pain, immunosuppressives, substances for the control of thrombosis, substances for the control or elimination of infection, peptides, proteins, human insulin or a human insulin analogue or derivative, polysaccharide, DNA, RNA, enzymes, antibodies, oligonucleotide, antiallergics, antihistamines, anti-inflammatories, corticosteroids, disease modifying anti-rheumatic drugs, erythropoietin, or vaccines, for use in the treatment or prevention of rheumatoid arthritis, psoriatic arthritis, ankylosing spondylitis, ulcerative colitis, hormone deficiency, toxicity, pain, thrombosis, infection, diabetes mellitus, diabetic retinopathy, acute coronary syndrome, angina, myocardial infarction, atherosclerosis, cancer, macular degeneration, allergy, hay fever, inflammation, anaemia, or myelodysplasia, or in the expression of protective immunity.

BRIEF DESCRIPTION OF THE DRAWINGS

Embodiments of the invention are further described hereinafter, by way of example only, with reference to the accompanying drawings, in which:

FIGS. 6 and 6A-6C illustrate incrementing the dose;

FIGS. 8 and 8A-8F illustrate dose delivery;

DETAILED DESCRIPTION

Figure 1:
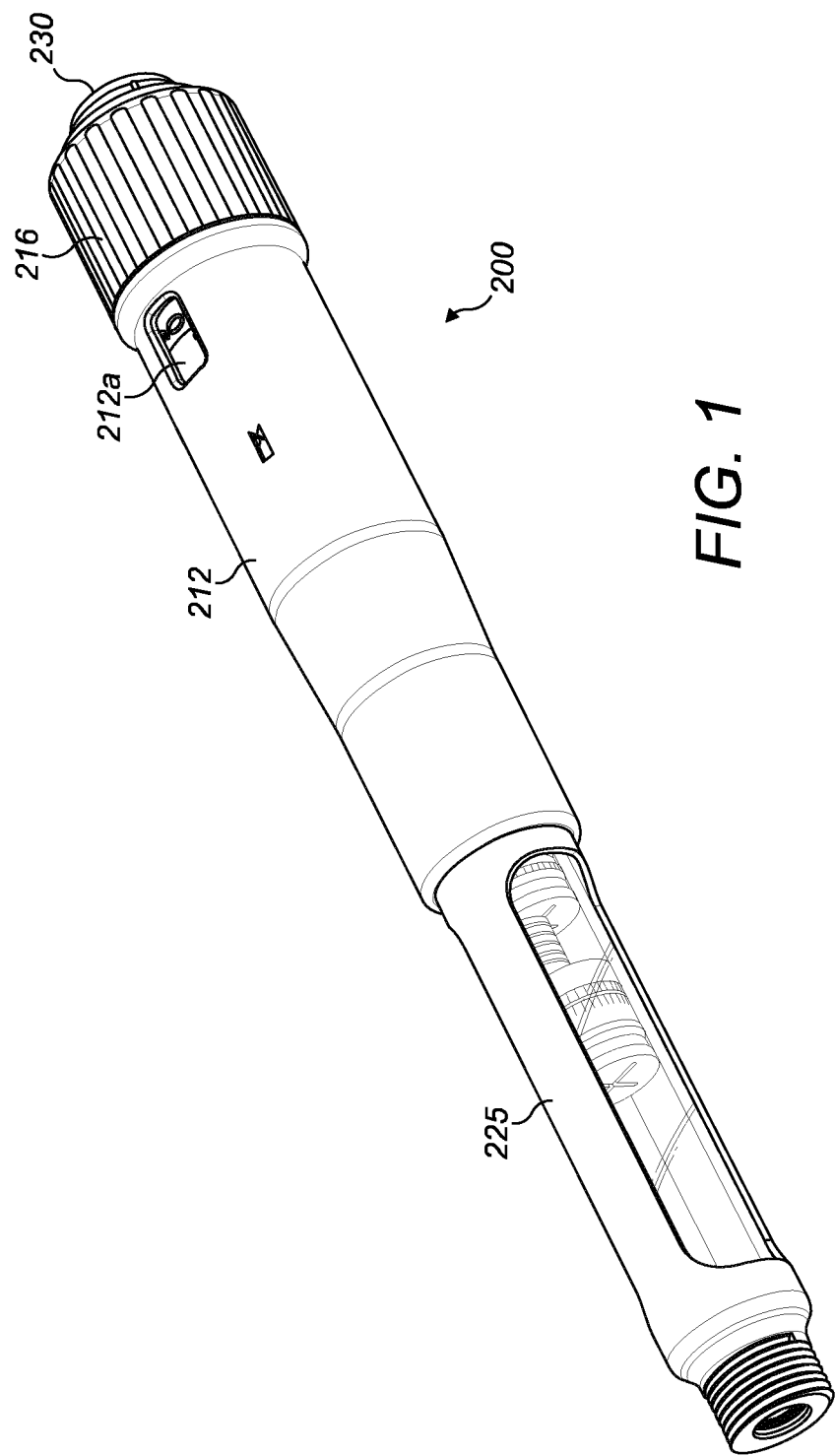
FIG. 1 is a perspective view of another embodiment of the injection device.

In the present disclosure, the following terms may be understood in view of the below explanations:

The term "injection device" may refer to a device intended for the injection of a medicament to the body and includes devices configured for various delivery methods, such as intradermal, subcutaneous, intramuscular, intravenous, intraosseous, intraperitoneal, intrathecal, epidural, intracardiac, intraarticular, intracavernous, and intravitreal, which may include via a cannula, catheter or similar device. Injection device includes syringes of all types, devices that contain said syringes such as auto-injectors, pen-injectors, patch injectors and other similar devices.

The term "pen-injector" may include any device configured to deliver a dose of a medicament from a cartridge.

The term "user" may refer to a medical practitioner, end user or other user associated therewith.

The term "coupling" may refer to a connection between components (not necessarily a direct connection; there may be intermediate components therebetween) that enables a force to be transmitted between the components;

The term "a rotational coupling" may refer to a coupling which enables a rotational force to be transmitted between the components;

The term "operatively connectable" may refer to at least two individual components which are releasably connectable together in such a way that the individual components can work together, for example wherein rotation of one of the individual components effects rotation of all of the operatively connected components;

The term "dose selector" may refer to a component or components which, when actuated by a user, enable a dose of medicament to be selected;

The term "dose indicator" may refer to a component or components which provide a display or indication to the user of the selected dose of medicament;

The term "splines" may refer to one or more ridges, ribs or other protrusions on one component which engage in corresponding grooves or the like on a second component to connect the two components together;

The term "a splined connection" may refer to a connection effected by one or more splines;

The term "forward" or "forwards" may refer to a direction towards the end of the injection device from which medicament is expelled;

The term "backward", "backwards", "rearwards" or "rearwardly" may refer to a direction away from the end of the injection device from which medicament is expelled;

The term "drive assembly" may refer to an assembly of components capable of using a driving force from, for example, a spring, to eject medicament from an injection device;

The term "backlash" may refer to a clearance caused by a gap between mechanical components.

The term "medicament" may refer to a substance in liquid or gas form. The medicament may be selected from the group comprising of: antipsychotic substances including risperidone, hormones, antitoxins, substances for the control of pain, immunosuppressives, substances for the control of thrombosis, substances for the control or elimination of infection, peptides, proteins, human insulin or a human insulin analogue or derivative, polysaccharide, DNA, RNA, enzymes, antibodies, oligonucleotide, antiallergics, antihistamines, anti-inflammatories, corticosteroids, disease modifying anti-rheumatic drugs, erythropoietin, or vaccines, for use in the treatment or prevention of rheumatoid arthritis, psoriatic arthritis, ankylosing spondylitis, ulcerative colitis, hormone deficiency, toxicity, pain, thrombosis, infection, diabetes mellitus, diabetic retinopathy, acute coronary syndrome, angina, myocardial infarction, atherosclerosis, cancer, macular degeneration, allergy, hay fever, inflammation, anaemia, or myelodysplasia, or in the expression of protective immunity.

The term "containing the medicament", when referring to the injection device, may refer to the medicament being contained within a suitable medicament container, such as a pre-filled syringe or cartridge, within the injection device.

The terms "rotationally locked to" or "rotationally locked with respect to" may refer to a prevention of relative rotational movement between two rotationally locked components i.e. substantially no relative rotational movement between two rotationally locked components is possible.

Description of Example Embodiment

A non-limiting embodiment of an injection device according to the present invention is illustrated in FIGS. 1-21.

Referring to FIGS. 1-5, the injection device 200 includes a housing 212, a dose selector 216, a dose button 230 and dose button spring 231, a units wheel 218, a tens wheel 219, a ratchet pawl 217, a housing top cap 221, an odometer shuttle lock 222, a drive spring 220, a drive sleeve 240, a last dose nut 241, a drive clutch 250, a drive clutch spring 251, a leadscrew nut 252, a leadscrew 253 and a thrust bearing 254, all located concentrically about a common longitudinal axis L. The axis L extends between a front end 200a and a rear end 200b of the injection device 200.

The injection device 200 has a medicament cartridge 224 supported in a cartridge holder 225 at the front end 200a of the injection device. A needle or needle hub unit (not shown) can be connected to the cartridge holder. The cartridge is sealed by an axially-moveable cartridge stopper 226 at its rear end.

The dose button 230 is biased rearwardly by the effect of the dose button spring 231 between the housing 212 and front end of the drive sleeve 240 with which the dose button 230 is axially engaged. The dose selector 216 is provided at the rear end 200b of the injection device 200 and is arranged to permit the selection of a desired dose of medicament for delivery from the medicament cartridge 224 into an injection site. The dose selector 216 is axially constrained with respect to the housing 212 but is rotatable with respect thereto, about axis L. The dose selector 216 is used to set the dose by increasing the rotational preload of the drive spring 220 which is prevented from unwinding by the ratchet pawl 217 which engages between the housing 212 and the units wheel 218.

Figure 2:
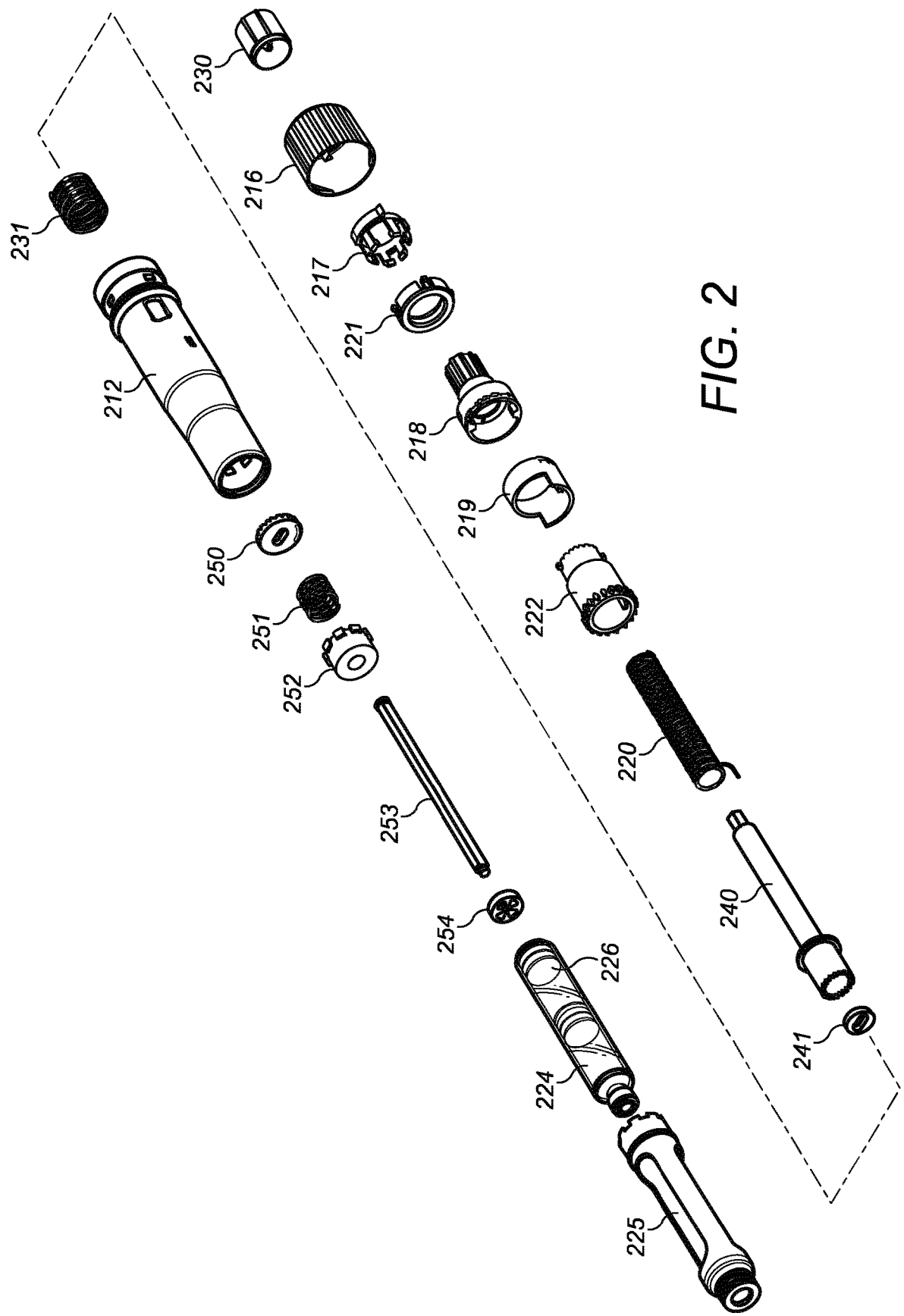
FIG. 2 is an exploded view of the injection device of FIG. 1.
Figure 2A:
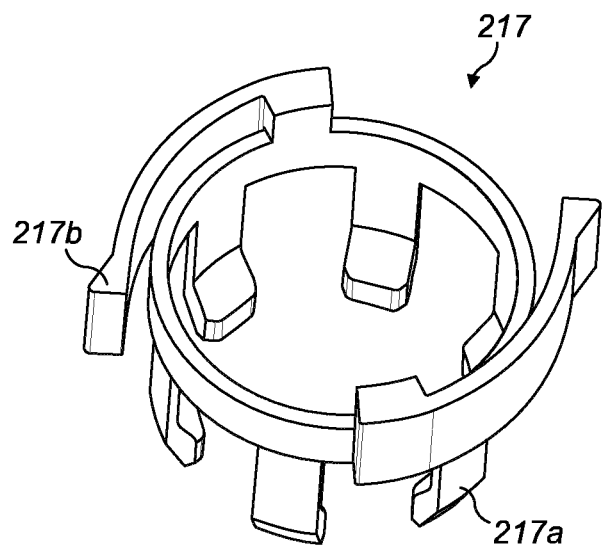
FIG. 2A is a perspective view of the ratchet pawl, drawn to a larger scale.

The ratchet pawl 217 (best seen in FIG. 2A) includes a plurality of ratchet fingers 217a which, in the assembled injection device 200, extend generally axially rearwardly to engage with the units wheel 218 as shown in FIG. 6C. The ratchet pawl 217 also includes ratchet arms 217b which, in the assembled injection device 200, engage with teeth 213 on the inside surface of the housing 212 to prevent unwinding of the drive spring 220, as shown in FIG. 6B, while the dose is being incremented.

A dose indicator is disposed within the housing 212 and displays reference indicia, such as numbers or symbols, to indicate the level of dose selected by the dose selector 216. The housing 212 includes an aperture 212a through which the dose indicator is visible. The dose indicator comprises the units wheel 218 for displaying units and the tens wheel 219 for displaying tens and the odometer shuttle lock 222. The units wheel 218 is intermittently coupled to the odometer shuttle lock 222 which is always rotationally coupled to the tens wheel 219. The tens wheel 219 has maximum and minimum dose limit features in the form of rotational endstops 271, 272 respectively, which can engage a limiting rib 290 in the housing 212 to keep the selected dose within the range defined by the maximum and minimum doses. This max/min dose limiting will be described in more detail later.

With reference to FIGS. 11-15, the dose indicator is an odometer comprising a units wheel 218, a tens wheel 219 and an odometer shuttle lock 222. The units wheel 218 has units numbers 260 around the circumference thereof, comprising two consecutive series of the numbers 0-9. Two drive dogs 261 are located 180 degrees apart on the internal surface of the forward end of the units wheel 218 and two engagement splines 262 are also located 180 degrees apart from one another. The sets of drive dogs 261 and engagement splines 262 may be rotationally offset from one another by approximately 90 degrees. In an alternative embodiment the units wheel 218 may comprise one consecutive series of the numbers 0-9 around its circumferential surface, and one drive dog 261. The units wheel 218 may comprise one or more than two engagement splines 262, the engagement splines 262 rotationally arranged to be engageable with the shuttle lock rear teeth 283. The drive dogs 261 have angled faces which, when engaging corresponding angled faces 282 on the shuttle lock 222, cause a camming action that can move the shuttle lock 222 axially.

Tens wheel 219 has tens numbers 270 around the circumference thereof, comprising a series of the numbers 0-10. The forward end of the tens wheel 219 includes maximum and minimum dose limit features 271, 272, in the form of rotary endstops which can each engage a max/min limit rib 290 on the internal surface of the housing 212. The internal surface of the tens wheel 219 includes a key 273 for engaging with the shuttle lock 222.

The shuttle lock 222 is a generally cylindrical component having a forward section of largest diameter with double-ended peripheral teeth 280 at the forward end thereof having angled faces which can alternately engage dogs 291 and engagement ribs 292 on the interior of the housing 212. The angled faces cause a camming action that can move the shuttle lock 222 axially.

In general terms, the function of the housing dogs 291, housing engagement ribs 292 and units wheel drive dogs 261 is to enable the shuttle lock 222 to move alternately between two axial positions, as will be explained in more detail later.

An axially-extending keyway 281 is provided for engaging the key 273 on the tens wheel 219 in order to rotationally lock the tens wheel 219 and shuttle lock 222 together whilst permitting axial movement therebetween. In alternative embodiments, the key may be provided on the shuttle lock 222 and the axially-extending keyway may be provided on the tens wheel 219.

The rear section of the shuttle lock 222 is of smaller diameter and includes dogs 282 at the rear end thereof, located 180 degrees apart from one another which can engage with the drive dogs 261 of the units wheel 218.

The rear surface of the shuttle lock 222 is provided with a series of axially-extending shuttle lock rear teeth 283. The number of teeth 283 corresponds with the number of units of medicament available per rotation of the units wheel 218 (in this case 20). Depending upon the relative axial positions of the units wheel 218 and the shuttle lock 222, the engagement splines 262 on the units wheel 218 can either be engaged with the shuttle lock rear teeth 283, or not engaged with the shuttle lock rear teeth 283.

Figure 15:
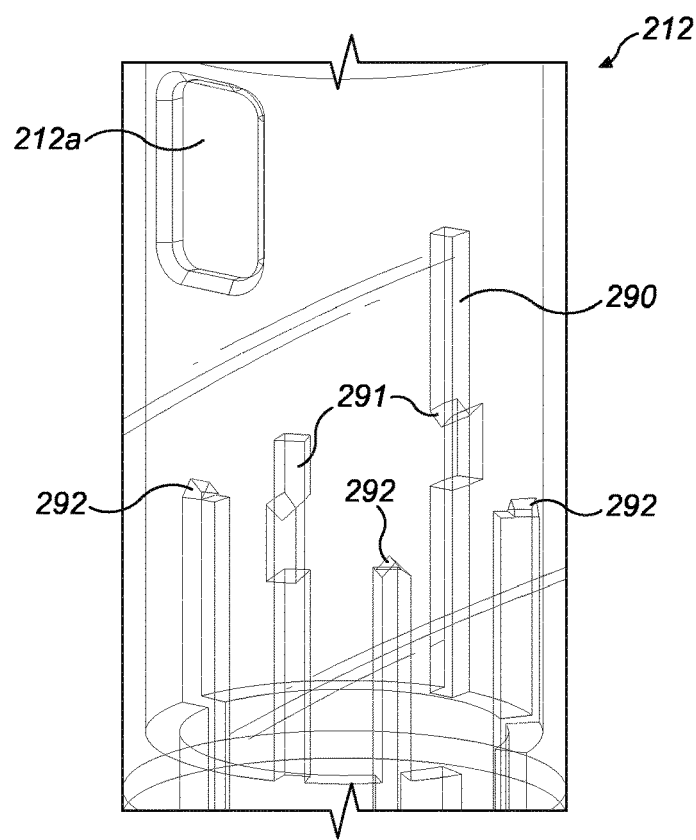
FIG. 15 is a perspective view of housing features relevant to the odometer mechanism.

FIG. 15 shows the portion of the internal surface of the housing 212 which interacts with the odometer mechanism. The aperture 212a through which the dose is displayed can be seen. The illustrated portion of the housing includes an internally-projecting max/min limit rib 290, two dogs 291 for engaging the shuttle lock 222 and three engagement ribs 292 for engaging the shuttle lock 222. FIG. 15 is shown partly in cross-section; the pointed ends of dogs 291 are at the same axial position and are located 180 degrees apart on the internal surface of the housing 212 (half of the housing 212 has been removed from FIG. 15).

As illustrated in FIG. 15, one of the dogs 291 for engaging the shuttle lock 222 may be located at one end of the max/min limit rib 290 such that both functions can be performed by the same component on the internal surface of the housing 212.

The drive spring 220 is a torsion spring which is fixed at one end with respect to the housing 212 and engaged at its other end to the units wheel 218.

Figure 2B:
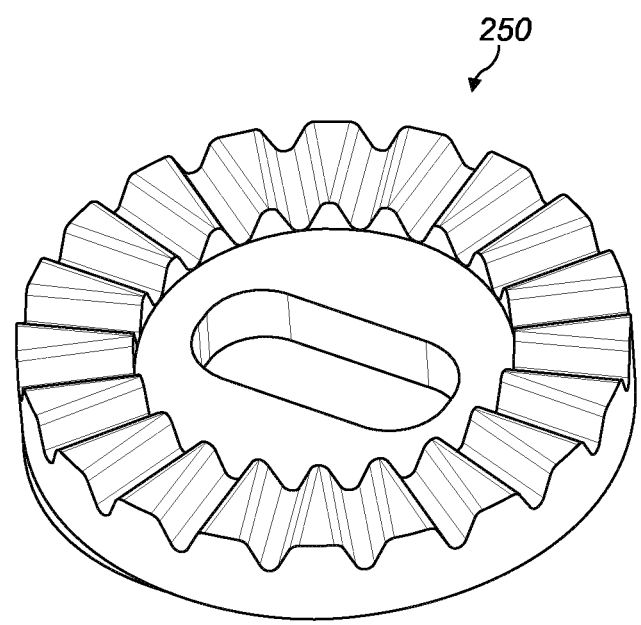
FIG. 2B is a perspective view of the drive clutch, drawn to a larger scale.
Figure 3:
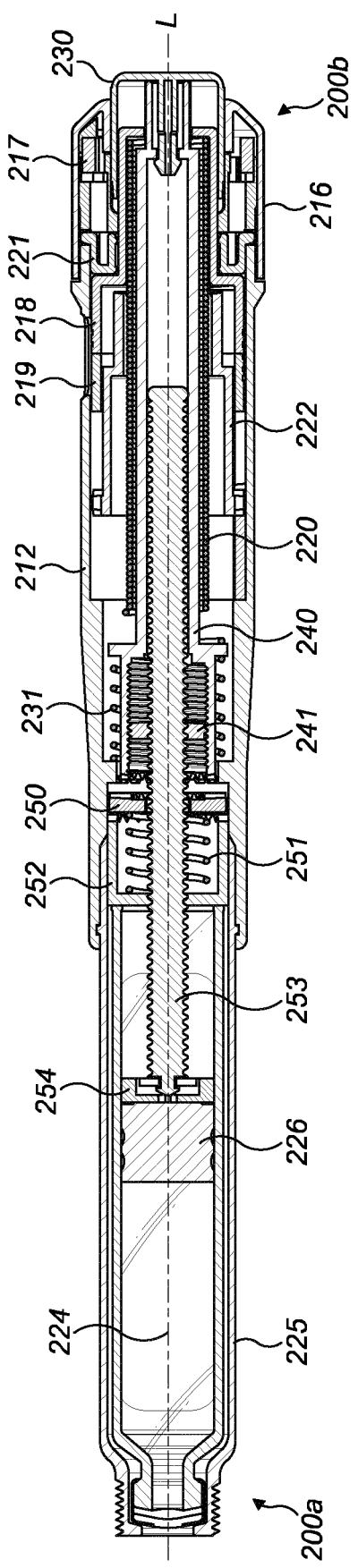
FIG. 3 is a cross-sectional view of the injection device of FIG. 1.
Figure 4:
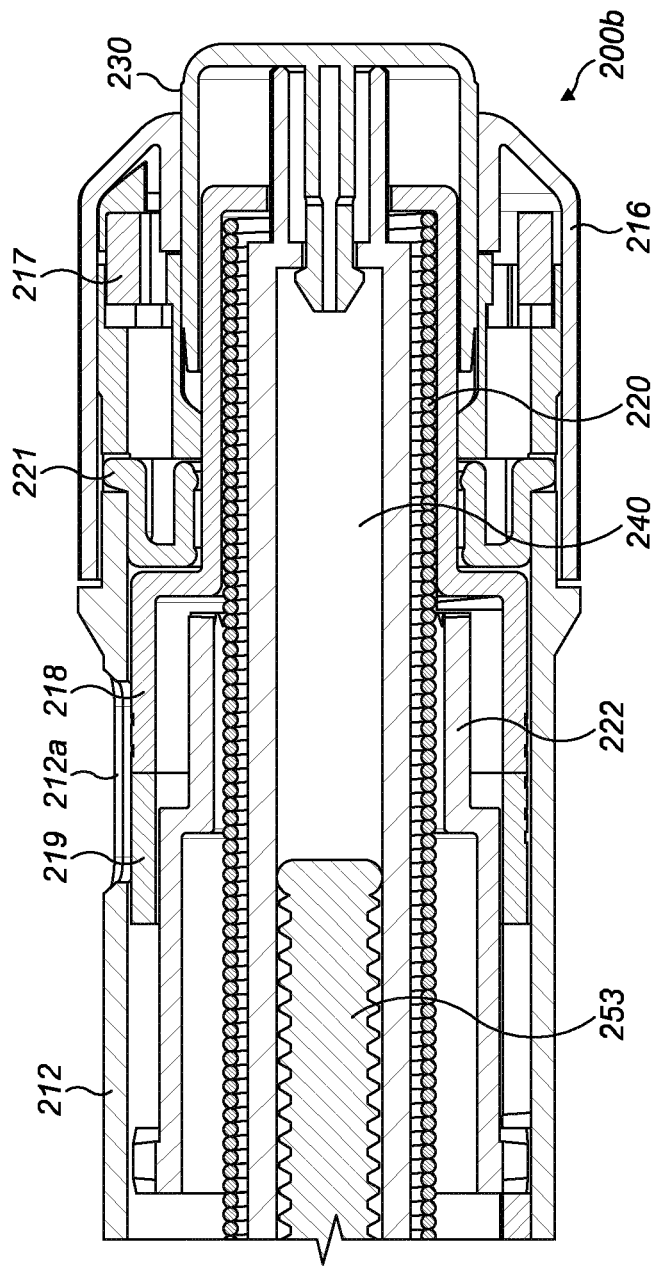
FIG. 4 is a cross-sectional view, drawn to a larger scale, of the rear end of the injection device of FIG. 1.
Figure 5:
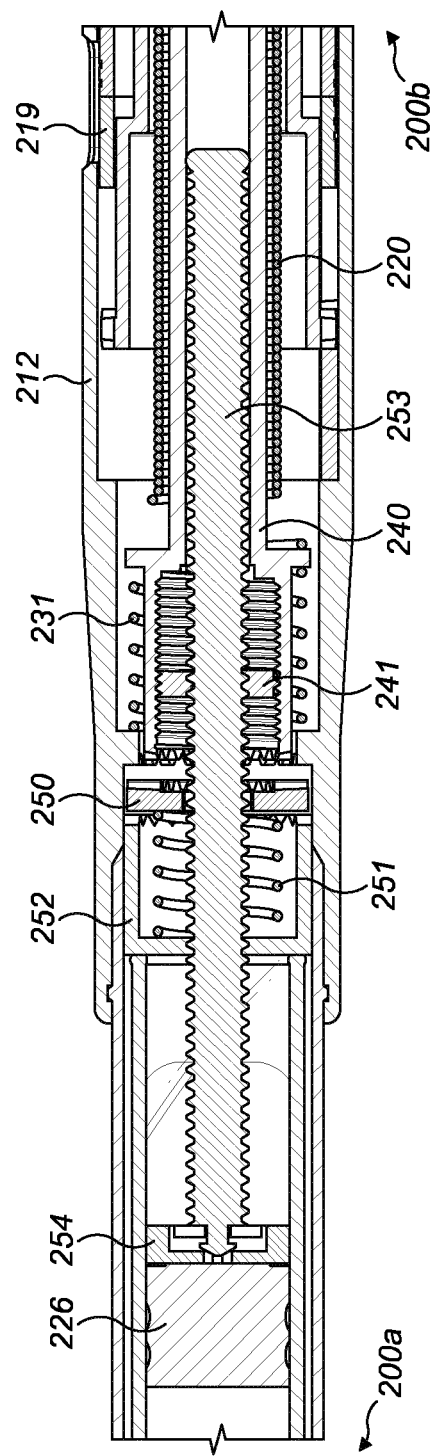
FIG. 5 is a cross-sectional view, drawn to a larger scale, of the central portion of the injection device of FIG. 1.

The drive clutch 250, best seen in FIG. 2B, is generally circular with formations (uppermost in FIG. 2B) which, in the assembled injection device 200, extend in a direction towards the rear of the device. The drive clutch spring 251 biases the medicament cartridge 224. The housing 212 is provided with forward-facing clutch engaging features 215 which, in the position shown in FIG. 6, engage the clutch 250 so that they are rotationally locked together. The clutch 250 can be disengaged from the clutch engaging features of the housing 215 by forward axial movement of the clutch 250, caused by forward movement of the drive sleeve 240. A haptic feedback arm 250a is provided on the front face of the drive clutch 250 (the underside in FIG. 2B).

The operation of the respective features of the injection device 200 will now be described in more detail below.

When the dose button 230 is depressed, firstly the drive clutch 250 is decoupled from the housing 212 and coupled to the drive sleeve 240. Secondly, the ratchet pawl 217 is decoupled from the units wheel 218. Decoupling of the ratchet pawl 217 from the units wheel 218 allows the drive spring 220 to rotate the units wheel 218 and drive sleeve 240, which are rotationally coupled together, about the longitudinal axis L.

Rotation of the drive sleeve 240 causes the drive clutch 250 to rotate which, in turn, rotates the leadscrew 253 to which the drive clutch 250 is splined.

Rotation of the leadscrew 253 causes it to advance axially forwards towards the front end 200a of the injection device 200 because of the engagement of the leadscrew thread with the thread of the leadscrew nut 252. The leadscrew nut 252 is rotationally and axially fixed with respect to the housing 212.

During dose setting, the last dose nut 241 is rotationally fixed with respect to the housing 212 via the leadscrew 253. The last dose nut 241 can translate axially up and down the thread inside the drive sleeve 240 due to rotation of the drive sleeve 240 when the dose is being set. Translation of the last dose nut 241 inside the drive sleeve 240 is limited by a rotational stop feature on the drive sleeve 240 which limits the travel of the last dose nut 241 to a position corresponding with the maximum dispense volume of the injection device 200.

During dose delivery, the drive sleeve 240, leadscrew 253 and last dose nut 241 all rotate together and there is no axial translation of the last dose nut 241 with respect to the drive sleeve 240.

Dose Setting—Incrementing the Dose

With the injection device 200 in the configuration shown in FIG. 6, the user grips the dose selector 216 and rotates it clockwise about axis L, with respect to the housing 212, in order to increment the dose and charge the drive spring 220. As the dose selector 216 is turned clockwise, the dose selector 216 is engaged with the ratchet pawl 217, causing it to rotate with the dose selector 216. The ratchet pawl 217 drives the units wheel 218 clockwise because of ratchet fingers 217a engaging ribs 218a of the units wheel 218, as shown in FIG. 6A. The drive spring 220 is hooked into the back of the units wheel 218 and is therefore tightened as the units wheel 218 is rotated. In other words, torque is transferred from the dose selector 216 to the drive spring 220 directly through the dose indicator, i.e. the units wheel 218.

While the dose is being incremented, the ratchet arms 217b on the ratchet pawl 217 engage with teeth 213 on the inside surface of the housing 212 to prevent un-winding of the drive spring 220, as shown in FIG. 6B.

When the dose selector 216 reaches a maximum, minimum or last dose limit, the ratchet fingers 217a flex radially outwardly and skip past the ribs 218a of the units wheel 218 (FIG. 6C).

Dose Setting—Decrementing the Dose

Figure 7:
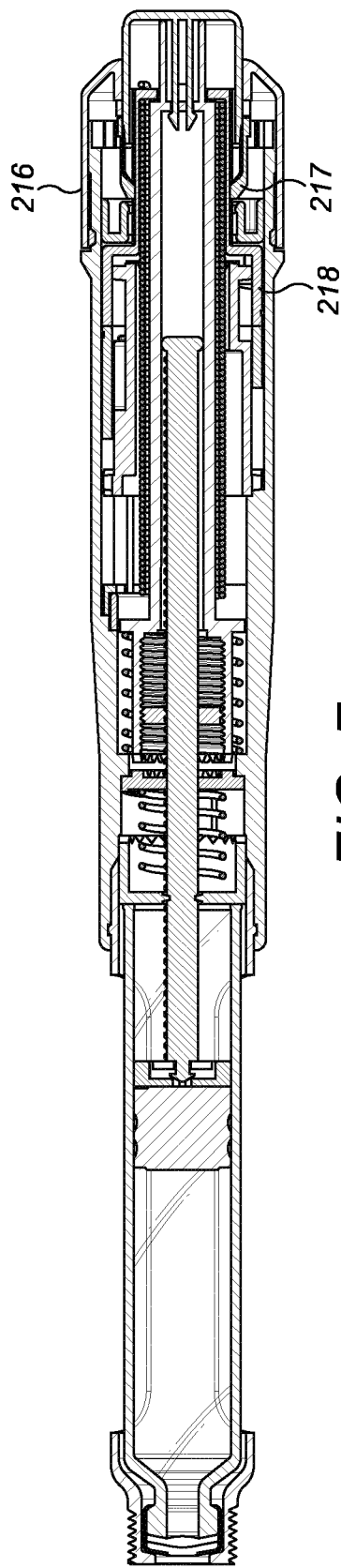
FIGS. 7, 7A and 7B illustrate decrementing the dose.
Figure 7B:
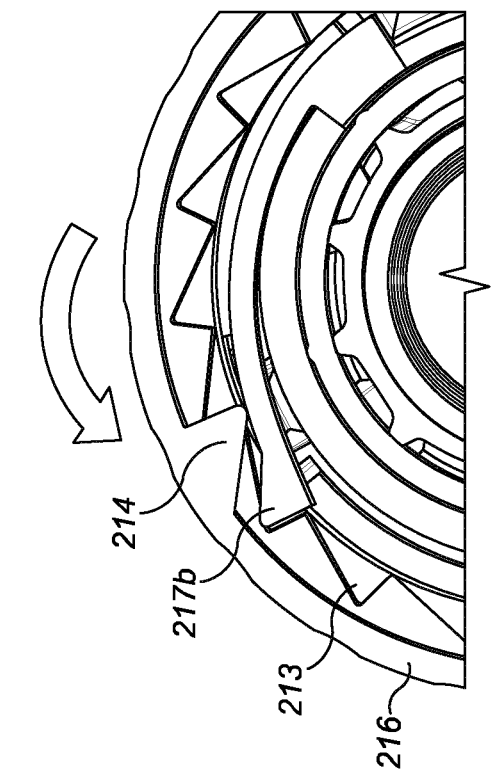
Figure 7A:
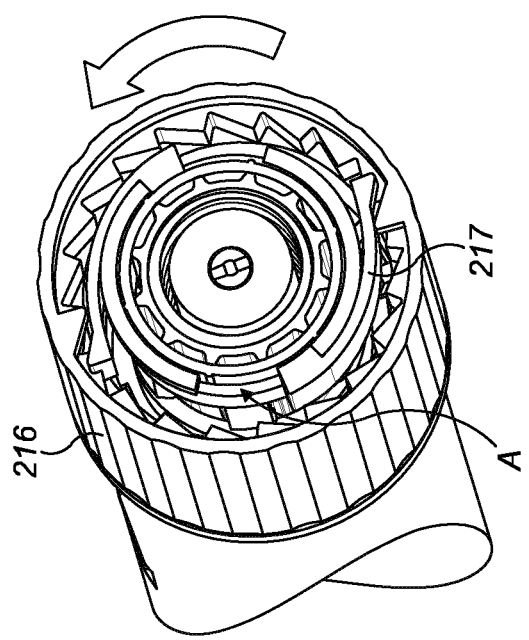

When it is desired to decrement the selected dose, the dose selector 216 is turned anti-clockwise. As shown in FIG. 7A, as the dose selector 216 is turned anti-clockwise, there is a small amount of backlash at point A such that the dose selector 216 can rotate slightly with respect to the ratchet pawl 217. This small relative movement is sufficient to allow tabs 214 on the dose selector 216 to depress the ratchet arms 217b so that they can click past the housing teeth 213, allowing the drive spring to unwind slightly before the ratchet arms 217b catch again on the next housing tooth 213. The tabs 214 may be tooth-shaped formations projecting radially-inwardly from an internal surface of the dose selector 216. This is represented in FIG. 7B. Each decrement preferably equates to 1 IU ("international unit") of medicament.

Dose Delivery

To initiate dose delivery, the user presses the dose button 230 against the bias of the dose button spring 231 as shown in FIG. 8. This pushes the drive sleeve 240 axially forwards. Although the drive sleeve 240 is rotationally locked to the units wheel 218, it is free to slide axially with respect thereto (FIG. 8B).

Figure 8D:
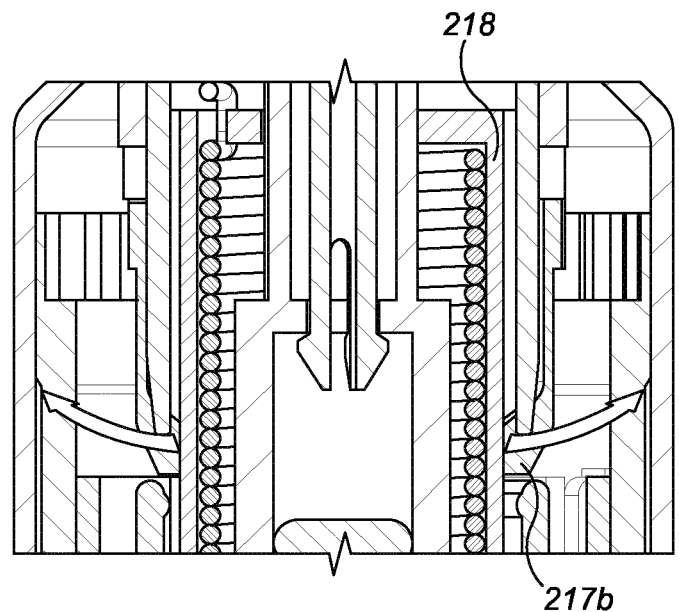
Figure 8E:
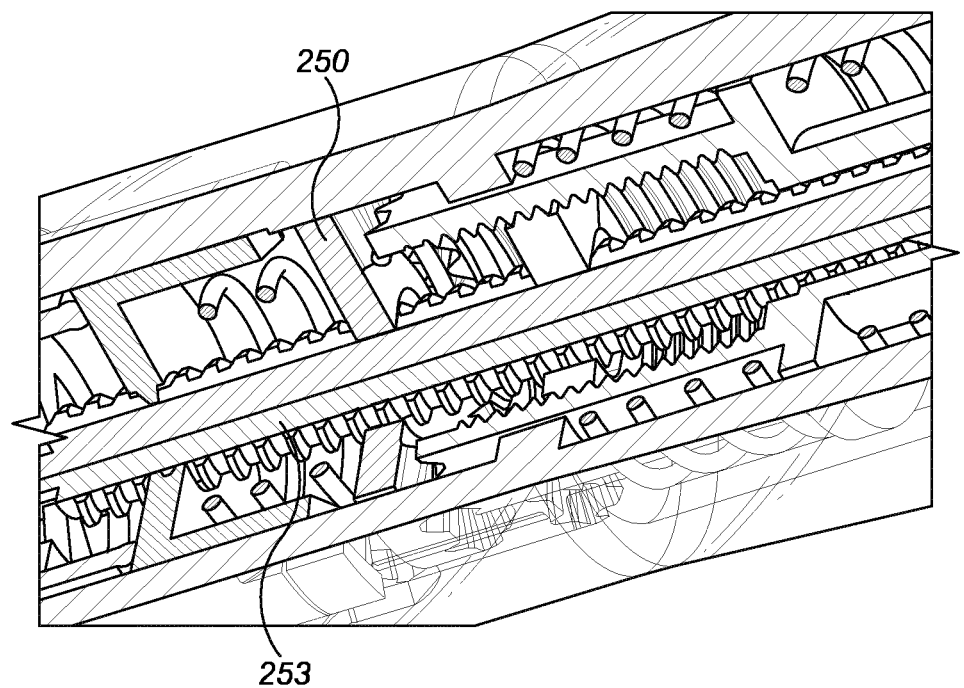

As the drive sleeve 240 advances, its forward end engages the rear surface of the drive clutch 250. The drive clutch 250 disengages from the clutch engaging features 215 on the inside surface of the housing 212 (FIG. 8C). Once the drive clutch 250 is fully engaged with the drive sleeve 240, the dose button 230 disengages the ratchet pawl 217 from the units wheel 218 (FIG. 8D). The units wheel 218 is now free to rotate the drive sleeve 240 and therefore also the drive clutch 250 about longitudinal axis L. The drive clutch 250 is splined to the leadscrew 253 (FIG. 8E).

Figure 8F:
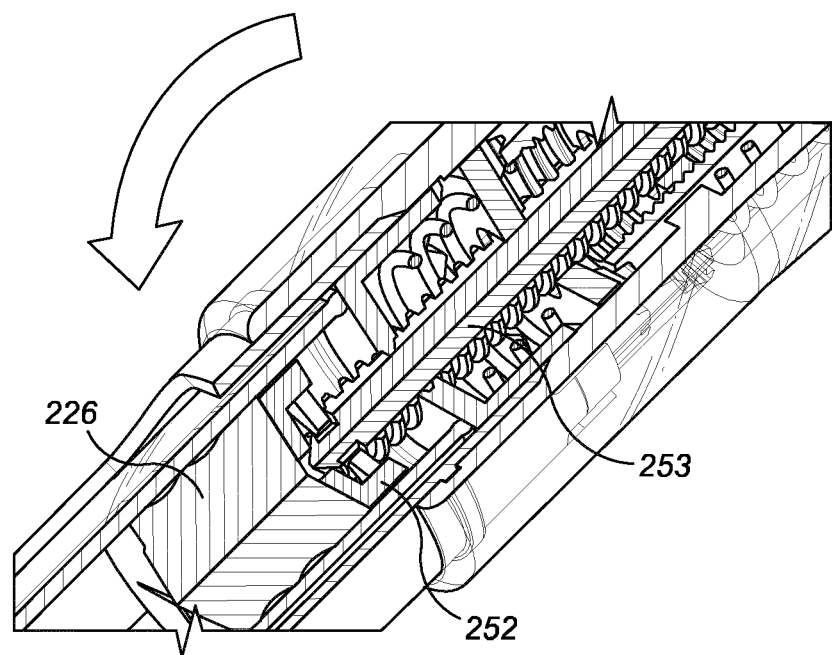

Therefore the leadscrew 253 now rotates and is caused to advance axially due to threaded engagement with the leadscrew nut 252. The thrust bearing 254 advances the cartridge stopper 226 into the cartridge, in order to expel medicament to deliver the selected dose (FIG. 8F).

When the dose button 230 is released, the dose button spring 231 returns the dose button 230 and drive sleeve 240 to their original starting positions. This axially rearward movement disengages the drive clutch 250 and re-engages the ratchet arms 217b with the housing 212 thereby stopping dose delivery.

Dose Delivery—Haptic Feedback

Figure 9:
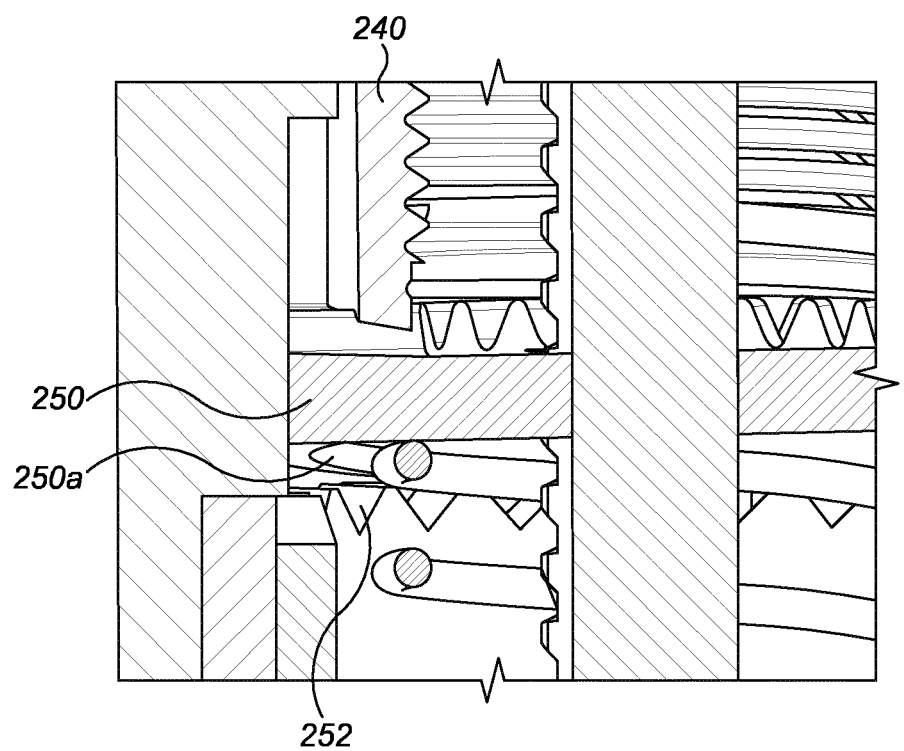
FIG. 9 illustrates a haptic feedback feature.

Referring to FIG. 9, during dose delivery haptic feedback occurs between the drive clutch 250 and the leadscrew nut 252 when the drive clutch 250 is spinning, by virtue of the haptic feedback arm 250a on the drive clutch clicking over axially-rearwardly-facing teeth on the leadscrew nut 252.

Last Dose Protection

When the medicament cartridge 224 is relatively empty, after several doses have already been delivered therefrom, it is undesirable for the user to be able to select a dose that is larger than the available quantity of medicament remaining. Last dose protection is provided to deal with this situation. Last dose protection is provided by the last dose nut 241.

Figure 10:
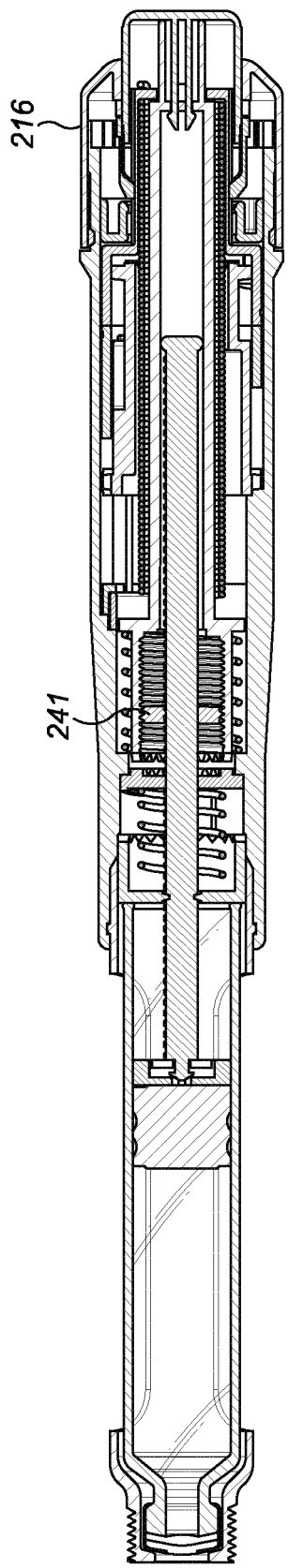
FIGS. 10, 10A and 10B illustrate last dose protection.
Figure 10B:
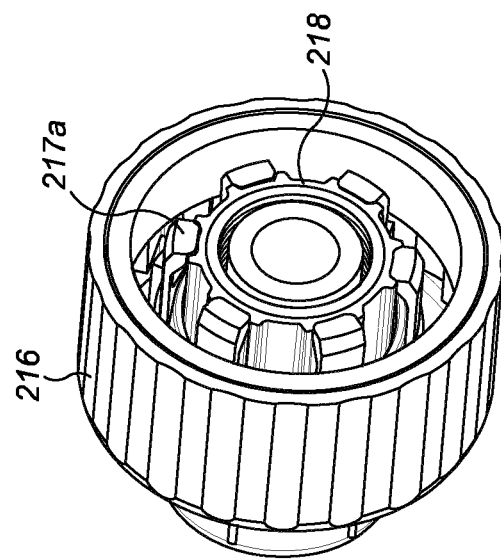
Figure 10A:
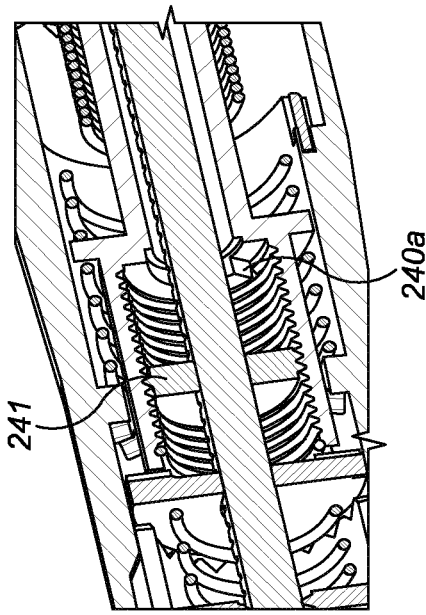
Figure 11:
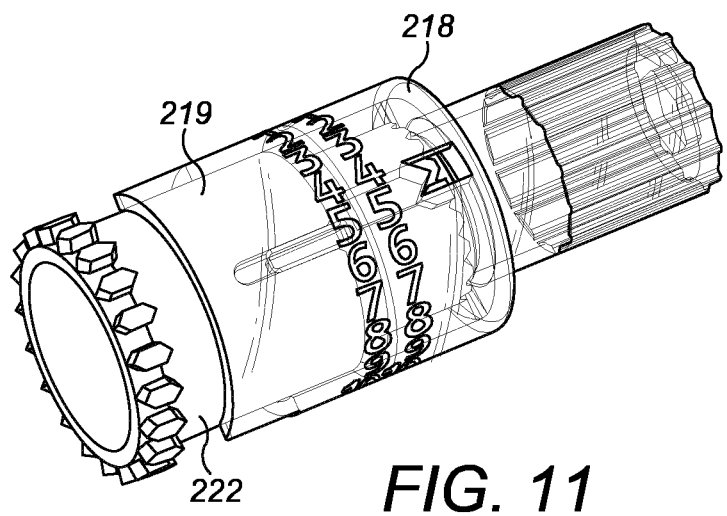
FIG. 11 is a perspective view of the odometer mechanism.
Figure 12:
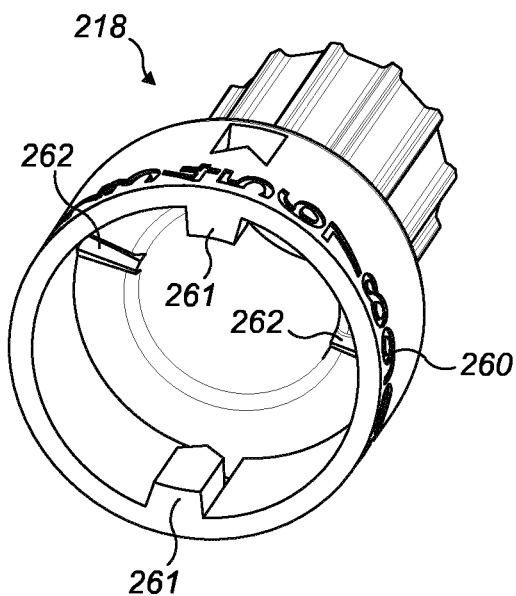
FIG. 12 is a perspective view of the units wheel from the odometer mechanism.
Figure 13:
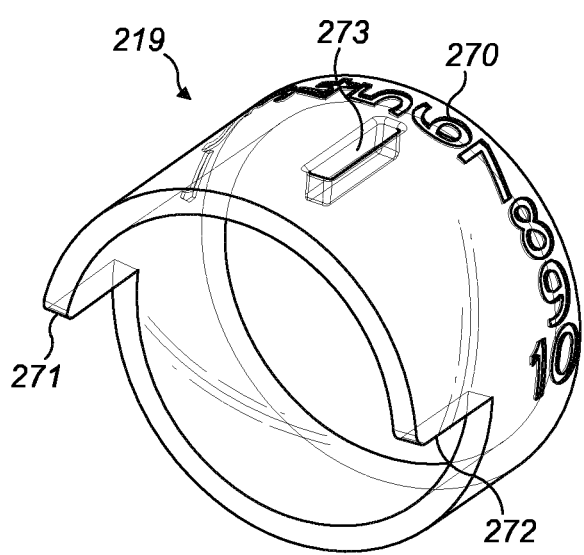
FIG. 13 is a perspective view of the tens wheel from the odometer mechanism.

As shown in FIG. 10A, the last dose nut 241 moves axially forwards and backwards on the thread inside the drive sleeve 240 during dose incrementing and decrementing. When there is less than a predetermined amount (e.g. 100 IU) of medicament remaining in the cartridge 224, the last dose nut 241 stops against a rotary endstop 240a at the rear of the drive sleeve thread.

Engagement of the last dose nut 241 with the endstop 240a means that, should the user attempt to wind the dose selector 216 beyond the remaining dose, the over-torque protection is actuated, preventing the user from damaging the device (FIG. 10B). The ratchet fingers 217a disengage from the units wheel 218 as previously described in relation to FIG. 6C.

Dose Display

Figure 16A:
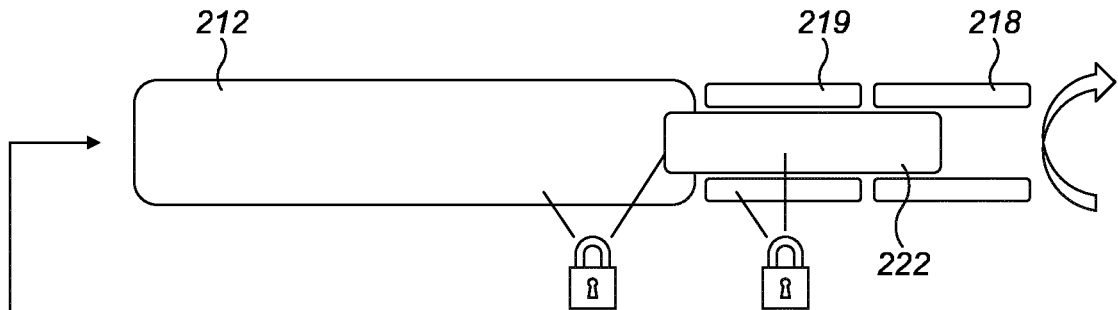
FIGS. 16A-16C show three stages of the odometer mechanism's operation.
Figure 16B:
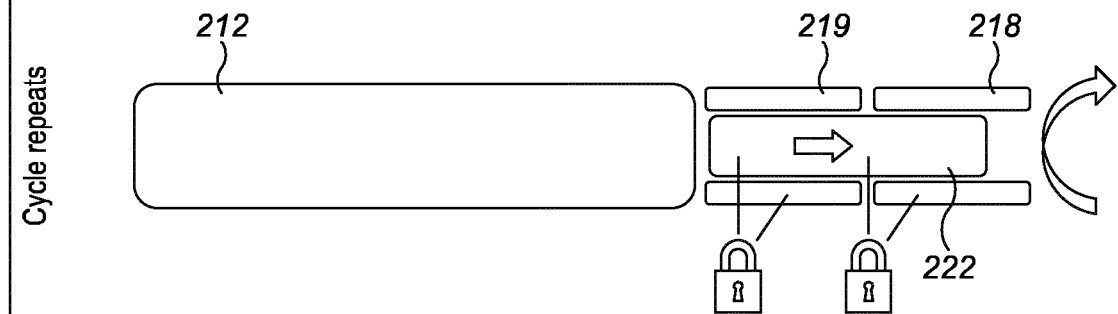
Figure 16C:
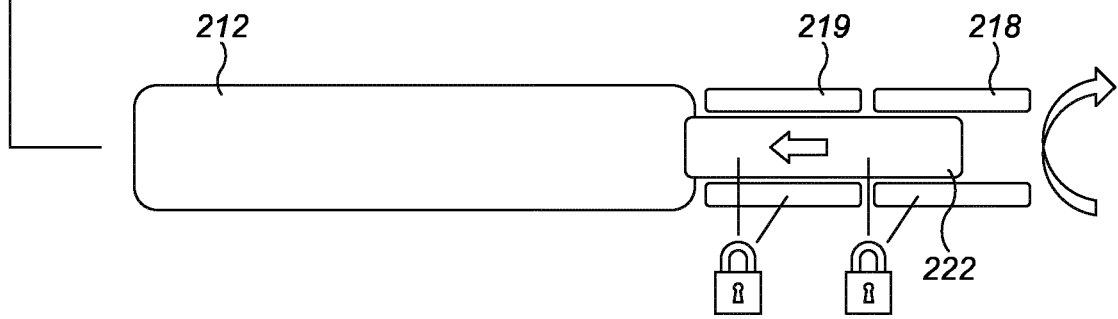
Figure 17:
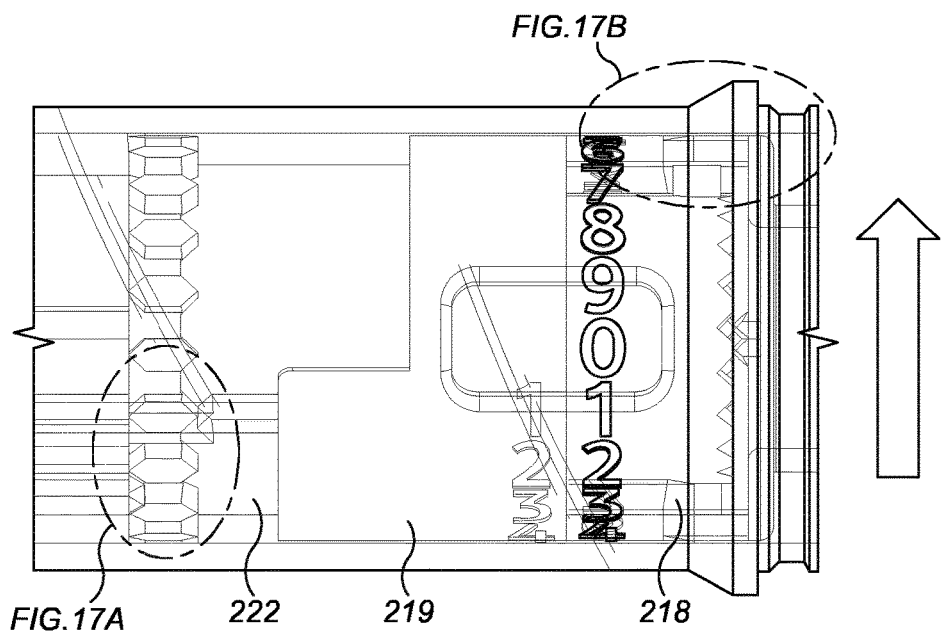
FIGS. 17, 17A and 17B show further detail of the stage illustrated in FIG. 16A.
Figure 18:
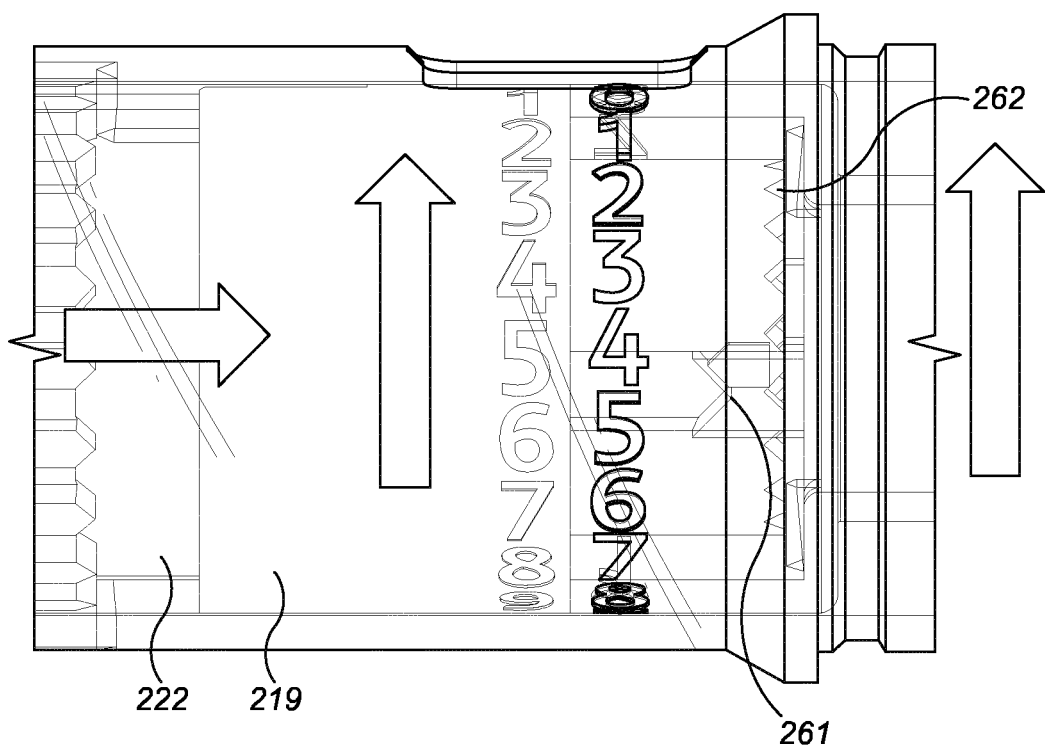
FIG. 18 shows further detail of the stage illustrated in FIG. 16B.
Figure 19:
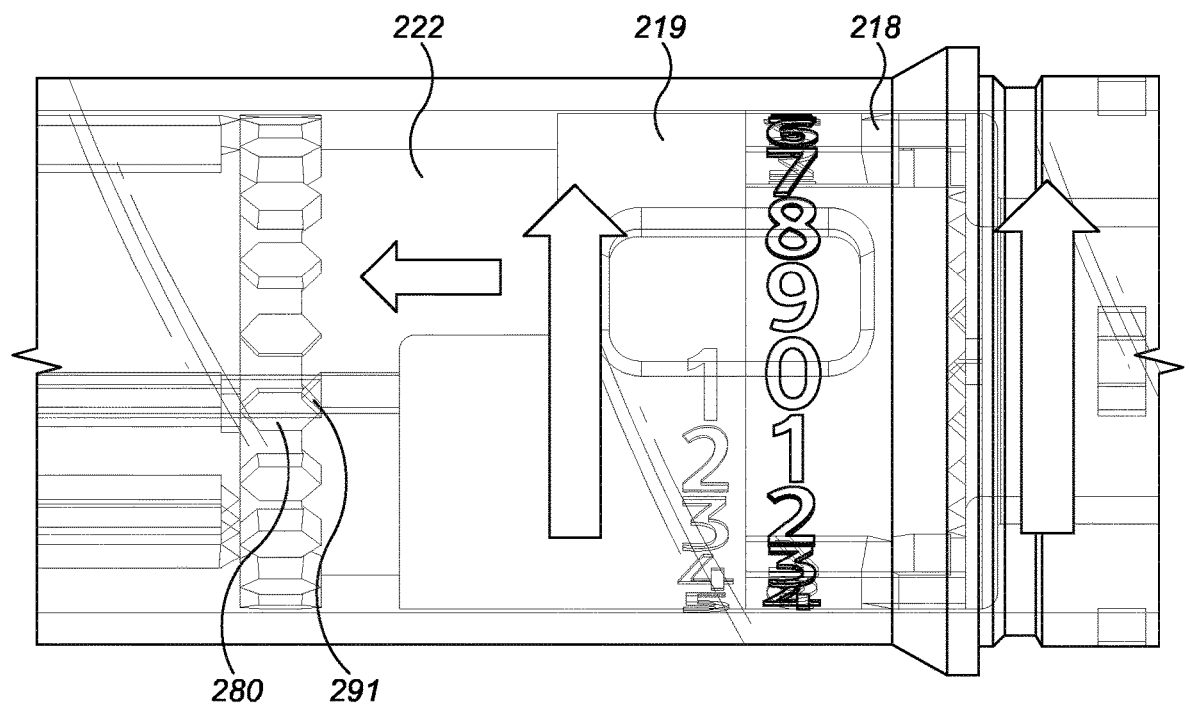
FIG. 19 shows further detail of the stage illustrated in FIG. 16C.

FIGS. 16A-16C show, in schematic form, the three stages of the odometer mechanism's operation. More detail of the respective stages is shown in FIGS. 17-19.

Figure 14:
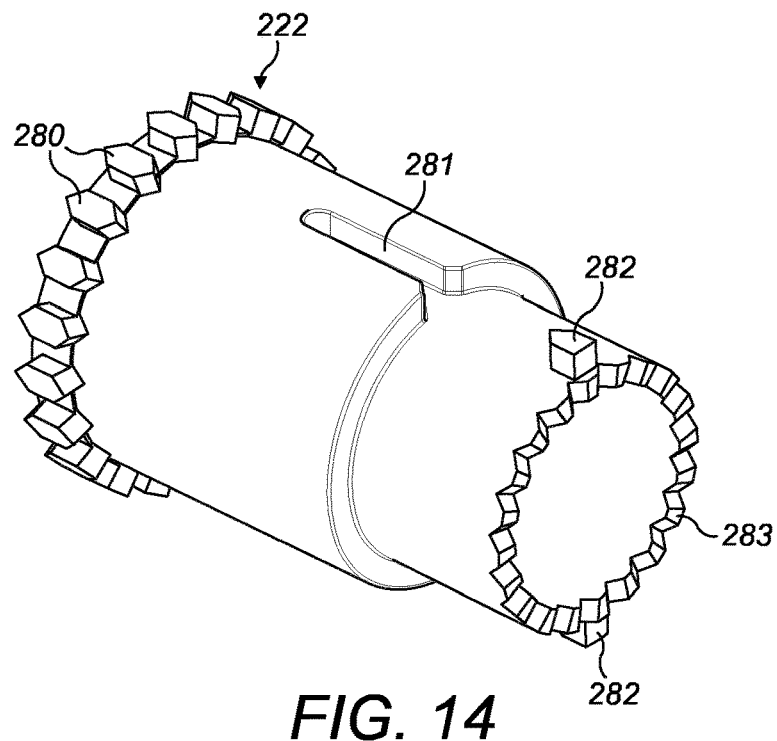
FIG. 14 is a perspective view of the shuttle lock from the odometer mechanism.
Figure 17A:
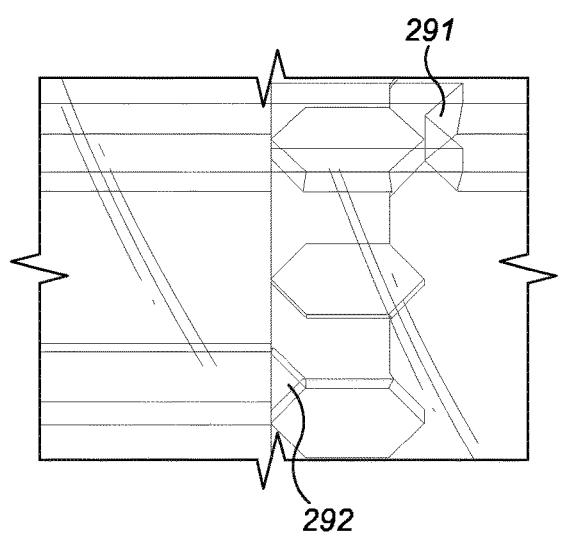
Figure 17B:
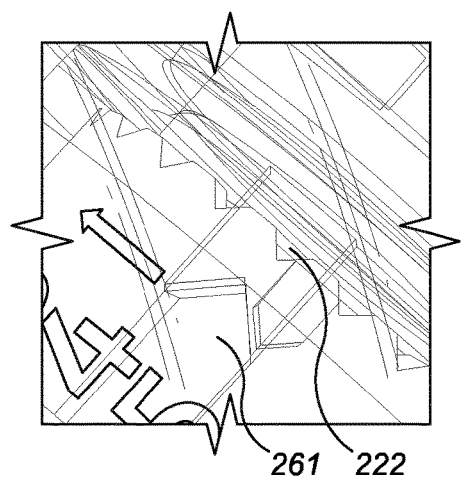

In stage 1 (FIGS. 16A, 17, 17A and 17B) for dose 0-9, the units wheel 218 is free to turn. Rotation of the dose selector 216 causes the dose to increment through doses 0-9. For doses 0-9, there is no engagement between the units wheel drive dogs 261 and the shuttle lock dogs 282 (FIG. 17B). The tens wheel 219 is rotationally locked but is axially moveable relative to the shuttle lock 222 because the key 273 is engaged in the keyway 281 (see FIG. 11). The shuttle lock 222 is rotationally locked to the housing 212 because the housing engagement ribs 292 (FIG. 17A) are engaged with three of the shuttle lock peripheral teeth 280 (FIG. 14).

After the units wheel has reached dose "9", in stage 2 (FIG. 16B and FIG. 18), the drive dogs 261 of the units wheel 218 engage shuttle lock dogs 282 during dose "10". The engagement of the angled faces of the dogs 261, 282, causes a camming action that moves the shuttle lock 222 axially rearwardly enough to disengage the shuttle lock peripheral teeth 280 from the housing engagement ribs 292. The shuttle lock 222 is therefore no longer rotationally locked to the housing 212. Since the key 273 is axially moveable in the keyway 281, the shuttle lock 222 is able to move axially relative to the tens wheel 219. Consequently, the tens wheel 219 itself does not move axially and the tens numbers 270 remain in a position adjacent to the units numbers 260. The axially rearward movement of the shuttle lock 222 causes angled faces of the dogs 261, 282 to reach the end of their sloping engagement, at which point the shuttle lock rear teeth 283 engage the axially-extending splines 262 on the units wheel 218. This rotationally locks the units wheel 218 and the shuttle lock 222 together.

The units wheel 218 is still able to turn. The tens wheel 219 is still rotationally locked to the shuttle lock 222 by virtue of the key 273 engaging in the keyway 281. Because the shuttle lock 222 (and hence the tens wheel 219 rotationally locked thereto) is rotationally locked to the units wheel 218 by the engagement of the units wheel splines 262 with the shuttle rear teeth 283, further turning of the units wheel 218 causes the shuttle lock 222 and the tens wheel 219 to rotate together.

After 9° of rotation of the shuttle lock 222 and tens wheel 219 by the units wheel 218, stage 3 is reached (FIG. 16C and FIG. 19), in which two of the shuttle lock peripheral teeth 280 come into contact with the angled faces of the two housing dogs 291.

Then, for the next 9° of rotation, the camming action of the angled faces of the housing dogs 291 and those of the shuttle lock peripheral teeth 280 cause the shuttle lock 222 to revert axially to re-engage the housing engagement ribs 292 so that the shuttle lock 222 is once again rotationally locked to the housing 212. Axial reversion of the shuttle lock 222 to its stage 1 forward position also causes the shuttle lock rear teeth 283 to disengage from the splines 262 on the units wheel 218. In this example, for every 18° of rotation (9°+9°), the shuttle lock completes a full cycle as described above. Other angles of rotation for each cycle are possible.

This completes the number change of the tens wheel 219. The mechanism functions in reverse if the dose is decremented.

Dose Setting—Maximum/Minimum Dose Limit

Figure 20A:
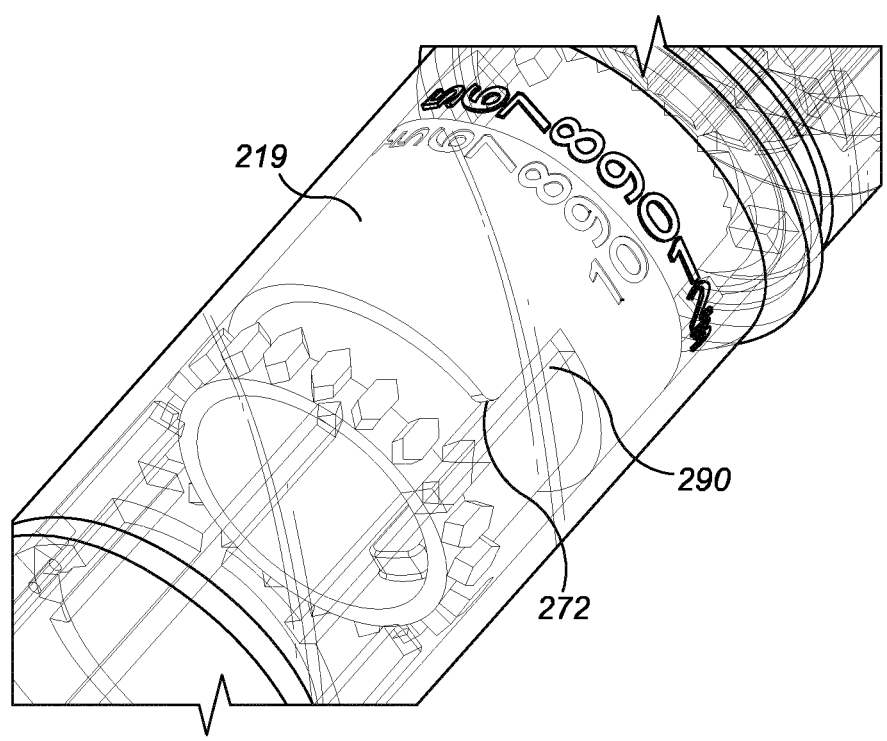
FIGS. 20A and 20B illustrate maximum/minimum dose limiting.
Figure 20B:
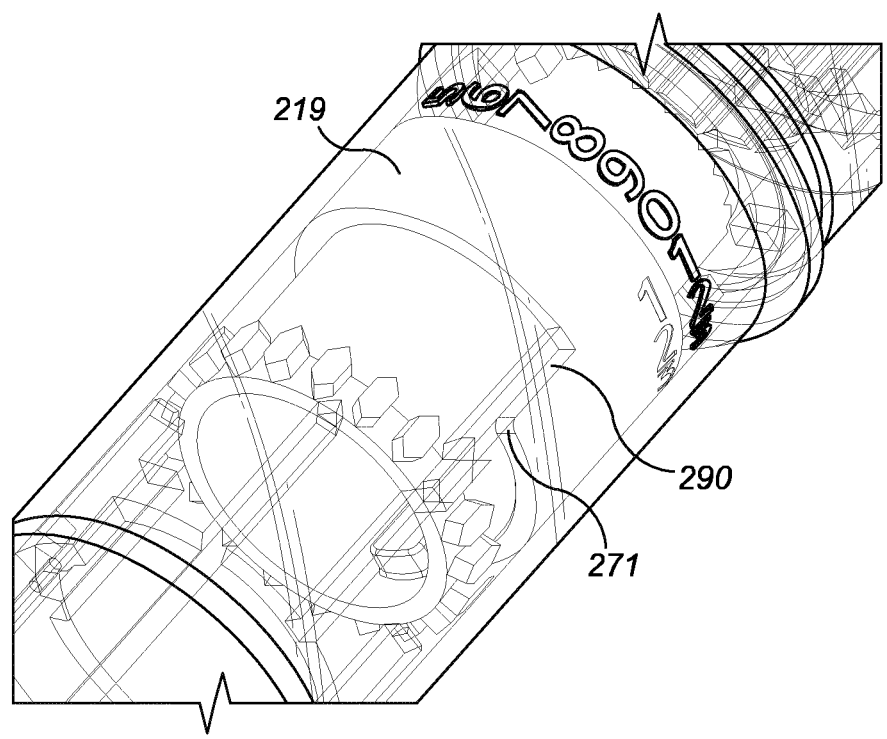

Limiting the maximum/minimum dose that can be set by the dose selector 216 is realised by cut out features 271, 272 on the tens wheel 219 which interact with a limit rib 290 on the housing. One side of the rib 290 limits the tens wheel at the minimum dose when feature 272 is rotated into abutment with the rib 290 (FIG. 20A). The other side of the rib 290 limits the tens wheel at the maximum dose, typically 100 IU, when feature 271 is rotated into abutment with the rib 290 (FIG. 20B). As mentioned above, the rib 290 is an extended part of one of the housing dogs 291 for engaging the shuttle lock 222.

Figure 21:
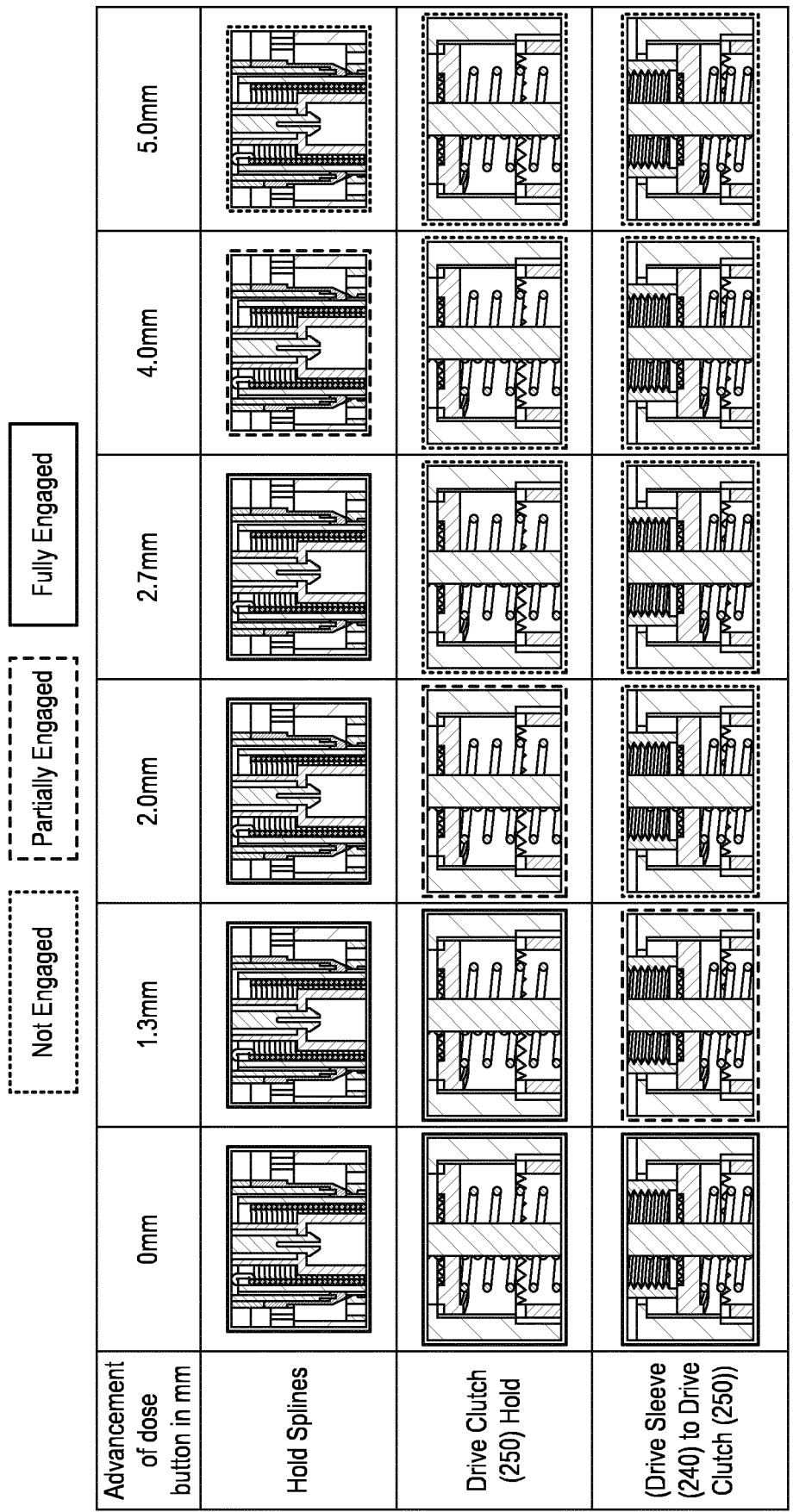
FIG. 21 is a diagrammatic summary of the key engagement points of the components of the injection device of FIG. 1, at six stages of dose delivery.

FIG. 21 is a diagrammatic summary of the key engagement points of the injection device components, at six stages of dose delivery. Example distances of advancement of the dose button 230, starting at 0 mm, are shown. For each distance, each of the hold splines (ratchet pawls 217), drive clutch 250 and drive sleeve 240/drive clutch 250 are indicated as being either not engaged (dotted box outline), partially engaged (dashed box outline) or fully engaged (solid box outline).

In summary, in this example embodiment, the dose indicator comprises an odometer including:
i. a units wheel 218 operatively connected to the dose selector 216 so that rotation of the dose selector 216 also rotates the units wheel 218, and
ii. a tens wheel 219 selectively engageable with the units wheel 218 so that rotation of the units wheel 218 also rotates the tens wheel 219,
wherein the dose indicator further comprises an axially-moveable shuttle lock 222 rotationally locked to the tens wheel 219 and selectively engageable with the units wheel 218 and the housing 212;
wherein the tens wheel 219 is selectively engageable with the units wheel 218 via said shuttle lock 222; and
wherein, when the tens wheel 219 is not engaged with the units wheel 218, the shuttle lock 222 is rotationally locked to the housing 212.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments.

The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

REFERENCE NUMERALS 200 injection device
200a front end of the device
200b rear end of the device
L longitudinal axis
212 housing
212a aperture in housing
213 housing teeth
214 tabs on housing
215 clutch engaging feature on housing
216 dose selector
217 ratchet pawl
217a ratchet fingers
217b ratchet arms
218 units wheel
218a units wheel ribs
219 tens wheel
220 drive spring
221 housing top cap
222 odometer shuttle lock
224 medicament cartridge
225 cartridge holder
226 cartridge stopper
230 dose button
231 dose button spring
240 drive sleeve
240a last dose nut endstop
241 last dose nut
250 drive clutch
250a haptic feedback arm
251 drive clutch spring
252 leadscrew nut
253 leadscrew
254 thrust bearing
260 units numbers
261 units wheel drive dogs
262 units wheel engagement splines
270 tens numbers
271 max dose limit feature
272 min dose limit feature
273 tens wheel key to engage shuttle lock
280 shuttle lock peripheral teeth
281 shuttle lock keyway
282 shuttle lock dogs
283 shuttle lock rear teeth
290 housing max/min limit rib
291 housing dogs for engaging shuttle lock
292 housing engagement ribs
A backlash point for dose decrementing

The invention claimed is:

1. An injection device comprising:
a. a housing having a longitudinal axis;
b. a dose indicator positioned within the housing; and
c. a dose selector operatively connectable to the dose indicator, the dose selector and the dose indicator being capable of cooperating with one another to set a dose to be ejected from the injection device,
wherein the dose indicator comprises an odometer including:
i. a units wheel operatively connected to the dose selector so that rotation of the dose selector also rotates the units wheel, and
ii. a tens wheel selectively engageable with the units wheel so that rotation of the units wheel also rotates the tens wheel,
wherein the dose indicator further comprises an axially-moveable shuttle lock rotationally locked to the tens wheel and selectively engageable with the units wheel and the housing along the longitudinal axis;
wherein the tens wheel is selectively engageable with the units wheel via said shuttle lock; and
wherein, when the tens wheel is not engaged with the units wheel, the shuttle lock is rotationally locked to the housing.

2. The injection device of claim 1 wherein the shuttle lock is generally cylindrical, having a forward section and a rear section, the forward section having a greater diameter than a diameter of the rear section.

3. The injection device of claim 1 wherein one of the shuttle lock and tens wheel includes an axially-extending keyway and the other of the shuttle lock and tens wheel includes a radially projecting key for engaging in said keyway in order to rotationally lock the shuttle lock to the tens wheel.

4. The injection device of claim 3 wherein the shuttle lock and tens wheel are axially moveable with respect to one another when said key is engaged in said keyway.

5. The injection device of claim 1 wherein the shuttle lock includes a set of peripheral teeth arranged in one axial location on an outer surface thereof, the peripheral teeth being capable of selectively engaging one or more formations on an internal surface of the housing.

6. The injection device of claim 5 wherein the peripheral teeth are substantially equally spaced around a circumference of the shuttle lock at said axial location.

7. The injection device of claim 5 wherein the peripheral teeth each have a forward surface and a rear surface, the forward and rear surfaces being capable of engaging first and second formations respectively on the internal surface of the housing.

8. The injection device of claim 7 wherein said first formations comprise ribs for engaging the forward surface of said peripheral teeth and said second formations comprise dogs for engaging the rear surface of said peripheral teeth.

9. The injection device of claim 8 wherein, when the tens wheel is not engaged with the units wheel, the shuttle lock is rotationally locked to the housing by said ribs engaging the forward surface of said peripheral teeth.

10. The injection device of claim 1 wherein said units wheel includes a drive dog having a cam surface capable of selectively engaging a dog on said shuttle lock to effect axial movement of said shuttle lock.

11. The injection device of claim 1 wherein said units wheel includes an axially-extending spline capable of engaging teeth on an end surface of said shuttle lock so as to selectively rotationally lock the units wheel and shuttle lock together.

12. The injection device of claim 1 wherein the units wheel and tens wheel are each marked with a sequence of numbers or symbols, at least one of the numbers or symbols being visible through an aperture or window in the housing.

13. The injection device of claim 1 further comprising a medicament container.

14. The injection device of claim 13 wherein the medicament container comprises a pre-filled syringe or cartridge.

15. The injection device of claim 13 further comprising a medicament contained in the medicament container.

16. The injection device of claim 15 wherein the medicament is selected from the group comprising: antipsychotic substances including risperidone, hormones, antitoxins, substances for the control of pain, immunosuppressives, substances for the control of thrombosis, substances for the control or elimination of infection, peptides, proteins, human insulin or a human insulin analogue or derivative, polysaccharide, DNA, RNA, enzymes, antibodies, oligonucleotide, antiallergics, antihistamines, anti-inflammatories, corticosteroids, disease modifying anti-rheumatic drugs, erythropoietin, or vaccines, for use in the treatment or prevention of rheumatoid arthritis, psoriatic arthritis, ankylosing spondylitis, ulcerative colitis, hormone deficiency, toxicity, pain, thrombosis, infection, diabetes mellitus, diabetic retinopathy, acute coronary syndrome, angina, myocardial infarction, atherosclerosis, cancer, macular degeneration, allergy, hay fever, inflammation, anaemia, or myelodysplasia, or in the expression of protective immunity.

17. An injection device comprising:
  a. a housing;
  b. a dose indicator positioned within the housing; and
  c. a dose selector operatively connectable to the dose indicator, the dose selector and the dose indicator being capable of cooperating with one another to set a dose to be ejected from the injection device,
wherein the dose indicator comprises an odometer including:
  i. a units wheel operatively connected to the dose selector so that rotation of the dose selector also rotates the units wheel, and
  ii. a tens wheel selectively engageable with the units wheel so that rotation of the units wheel also rotates the tens wheel,
wherein the dose indicator further comprises an axially-moveable shuttle lock rotationally locked to the tens wheel and selectively engageable with the units wheel and the housing;
wherein the tens wheel is selectively engageable with the units wheel via said shuttle lock; and
wherein, when the tens wheel is not engaged with the units wheel, the shuttle lock is rotationally locked to the housing,
wherein the internal surface of the housing further comprises an axially-extending rib for limiting rotation of the tens wheel.

18. The injection device of claim 17 wherein said tens wheel includes a rotary endstop feature for engaging said axially-extending rib.

19. The injection device of claim 18 wherein said tens wheel includes two of said rotary endstop features, for maximum and minimum dose limiting respectively.

20. The injection device of claim 19 wherein each of said rotary endstop features are capable of engaging said axially-extending rib.

* * * * *